(12) United States Patent
Sharma et al.

(10) Patent No.: US 7,559,451 B2
(45) Date of Patent: Jul. 14, 2009

(54) FULL THICKNESS RESECTIONING DEVICE

(75) Inventors: Satish K. Sharma, Randolph, MA (US);
David I. Freed, Westborough, MA (US);
Nicholas Patronik, Allston, MA (US);
Jeffrey M. Wendlandt, Newton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 385 days.

(21) Appl. No.: 11/192,575

(22) Filed: Jul. 29, 2005

(65) Prior Publication Data

US 2005/0263561 A1   Dec. 1, 2005

Related U.S. Application Data

(63) Continuation of application No. 10/731,652, filed on Dec. 9, 2003, now Pat. No. 6,938,814, which is a continuation of application No. 10/156,293, filed on May 24, 2002, now Pat. No. 6,685,079.

(51) Int. Cl.
*A61B 17/04* (2006.01)
(52) U.S. Cl. .................. 227/175.1; 227/19; 227/180.1
(58) Field of Classification Search .......... 227/175.1, 227/176.1, 180.1, 19; 600/119, 139, 140, 600/153
See application file for complete search history.

(56) References Cited

U.S. PATENT DOCUMENTS

| 4,671,445 | A | * | 6/1987 | Barker et al. | 227/19 |
| 6,119,913 | A | * | 9/2000 | Adams et al. | 227/176.1 |
| 6,126,058 | A | * | 10/2000 | Adams et al. | 227/180.1 |
| 6,685,079 | B2 | * | 2/2004 | Sharma et al. | 227/176.1 |
| 6,938,814 | B2 | * | 9/2005 | Sharma et al. | 227/176.1 |

FOREIGN PATENT DOCUMENTS

| EP | 0 668 057 | 8/1995 |
| WO | 2002/038037 | 5/2002 |

\* cited by examiner

*Primary Examiner*—Rinaldi I. Rada
*Assistant Examiner*—Nathaniel Chukwurah
(74) *Attorney, Agent, or Firm*—Fay Kaplun & Marcin, LLP

(57) ABSTRACT

A full thickness resection device comprises a control handle including an actuator wherein, when the device is in an operative position within a body lumen of a patient, the control handle remains outside the patient's body and a working head assembly coupled to a control handle by a flexible sheath, wherein, when the device is in the operative position; the working head assembly is located within a body lumen of the patient adjacent to a portion of tissue to be treated, the working head assembly including a tissue stapling mechanism including first and second tissue stapling members moveable relative to one another in combination with a first cable extending from the actuator through the flexible sheath to the first tissue stapling member so that, when the actuator is operated to draw the first cable proximally from the sheath, the first tissue stapling member is moved in a first direction relative to the second tissue stapling member.

2 Claims, 8 Drawing Sheets

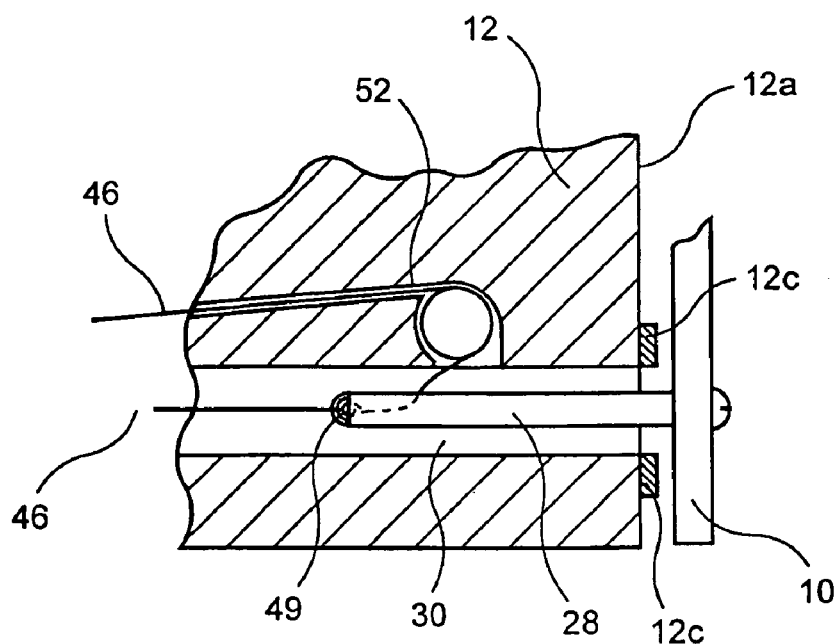
F I G. 5a
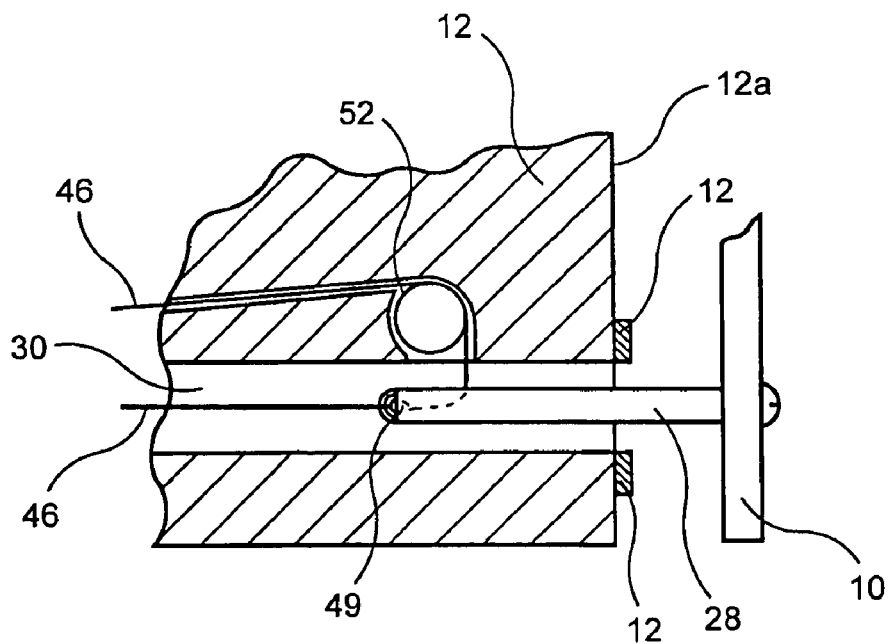
F I G. 5b

FULL THICKNESS RESECTIONING DEVICE

PRIORITY CLAIM

The present application is a continuation of a U.S. patent application Ser. No. 10/731,652 filed Dec. 9, 2003, now U.S. Pat. No. 6,938,814 entitled "Full Thickness Resectioning Device" which is a continuation of U.S. patent application Ser. No. 10/156,293, filed May 24, 2002, now U.S. Pat. No. 6,685,079, entitled "Full Thickness Resectioning Device". The entire disclosures of these prior applications, are considered as being part of the disclosure of the accompanying application and are hereby expressly incorporated by reference herein.

BACKGROUND INFORMATION

Full thickness resection procedures involve excising a full thickness portion of an organ, closing the hole created by the resection and removing the excess tissue.

Several known full thickness resection devices and procedures require at least one incision in an area near a portion of an organ to be excised to allow the physician to access the organ section to be excised and guide the device to that section. Those skilled in the art will understand that these incisions may add substantially to the patient discomfort and recovery time associated with the resectioning procedure itself.

SUMMARY OF THE INVENTION

The present invention is directed to a full thickness resection device comprising a control handle including an actuator wherein, when the device is in an operative position within a body lumen of a patient, the control handle remains outside the patient's body and a working head assembly coupled to a control handle by a flexible sheath, wherein, when the device is in the operative position; the working head assembly is located within a body lumen of the patient adjacent to a portion of tissue to be treated, the working head assembly including a tissue stapling mechanism including first and second tissue stapling members moveable relative to one another in combination with a first transmission member extending from the actuator through the flexible sheath to the first tissue stapling member so that, when the transmission member is operated, the first tissue stapling member is moved in a first direction relative to the second tissue stapling member.

BRIEF DESCRIPTION OF THE DRAWINGS

FIG. 5*a* shows a cross-sectional view of the working head assembly of FIG. 4 with the anvil member in a closed position;

FIG. 5*b* shows a cross-sectional view of the working head assembly of FIG. 4 with the anvil member in an open, tissue receiving position;

DETAILED DESCRIPTION

The present invention comprises a system for full thickness resection of tissue from within a body lumen including many features substantially similar to those described in U.S. patent application Ser. No. 09/694,894, filed Oct. 25, 2000 and entitled Method and Device for Full Thickness Resectioning of an Organ, the entire disclosure of which is hereby expressly incorporated by reference ("the '894 application). Those skilled in the art will understand that the working head assembly 2 described below may be constructed substantially in accord with any of the embodiments described in the '894 application except for the features specifically detailed below. Each of the embodiments described below reduces the length of the working head assembly required to enclose the drive mechanism for a tissue stapling apparatus.

Figure 1:
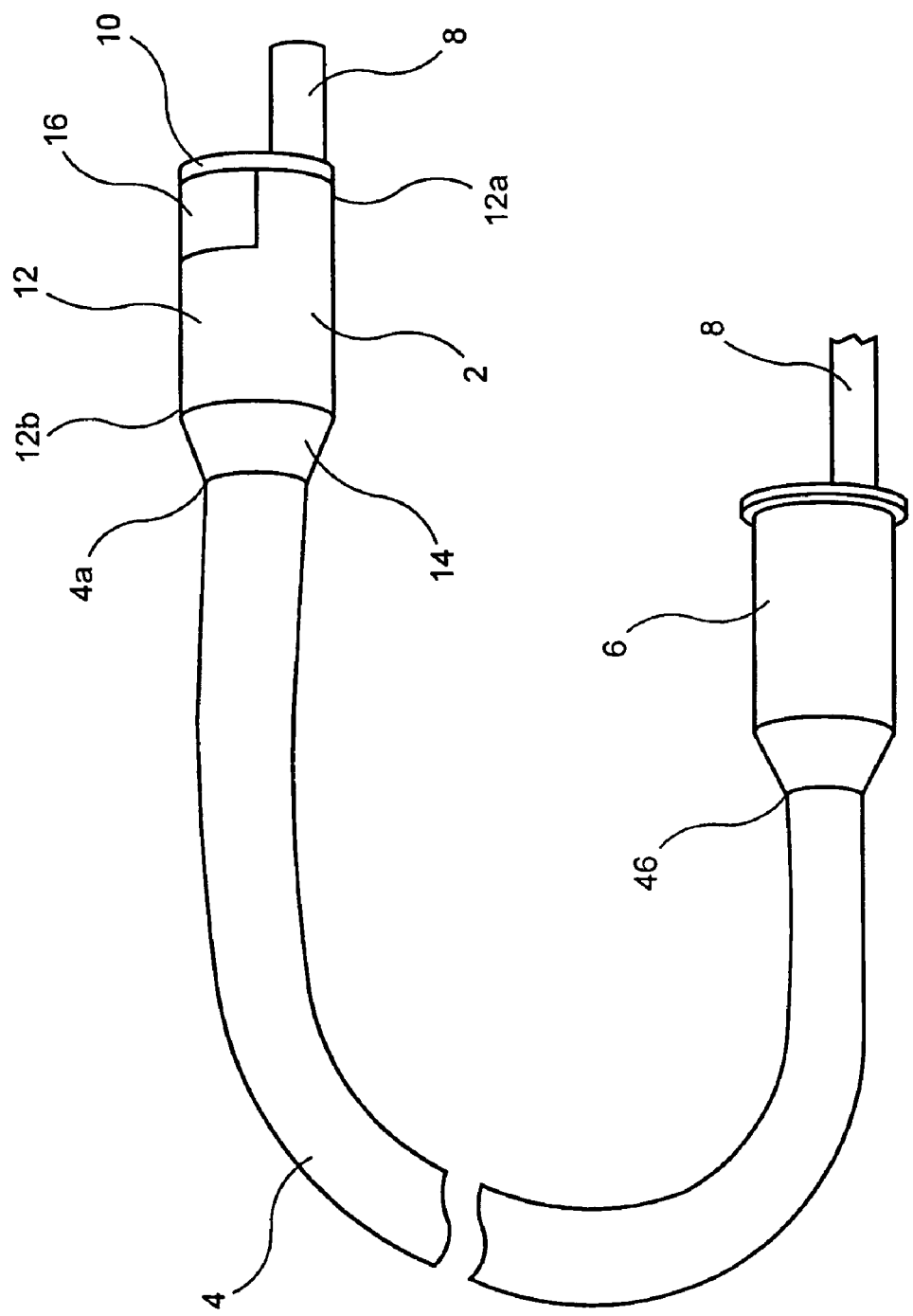
FIG. 1 shows a perspective view of a full thickness resection device according to a first embodiment of the present invention.
Figure 2:
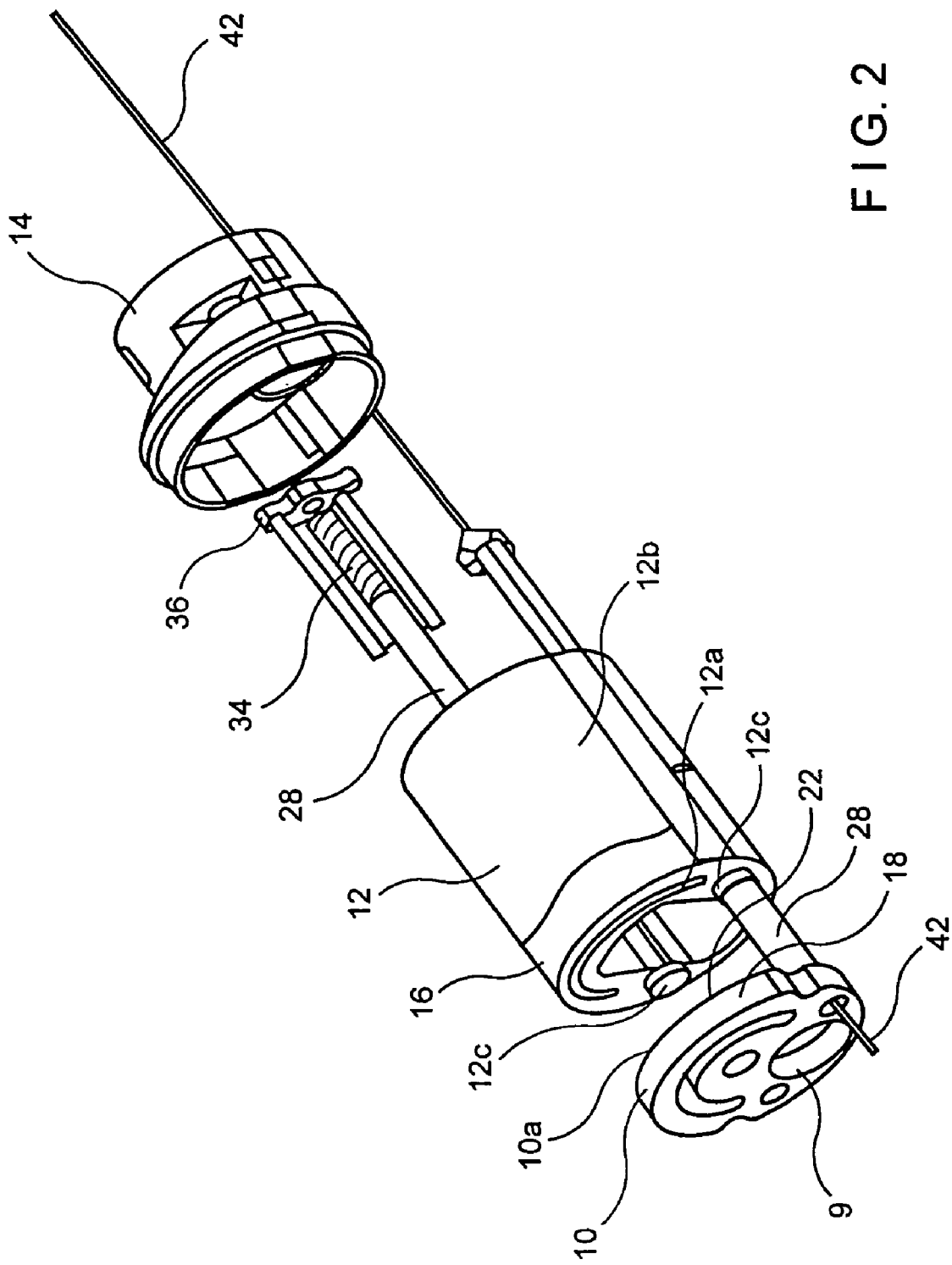
FIG. 2 shows a perspective view of a working head assembly of the device of FIG. 1.

As shown in FIGS. 1-3, an apparatus according to a first embodiment of the present invention comprises a working head assembly 2 which may preferably be connected to a distal end 4*a* of a sheath 4. The proximal end 4*b* of the sheath 4 may preferably be connected to a control handle 6 which remains outside the patient's body during operation.

In operation, the entire apparatus is mounted onto an endoscope 8 by passing the endoscope 8 through the control handle 6, the sheath 4, and through an endoscope receiving channel 9 in the working head assembly 2, as shown in FIGS. 1 and 2. The endoscope 8 is then inserted into an organ via a body orifice to locate a lesion under visual observation (usually while insufflating the organ). The organ may, for example, be a substantially tubular organ such as the colon. Once the lesion has been located, the working head assembly 2 and the sheath 4 are slidably advanced along the endoscope 8 into the organ until the working head assembly 2 is in a desired position adjacent to the lesion. Those skilled in the art will understand that a device according to the present invention may also be inserted into a body lumen via a surgically created opening.

As shown in FIG. 2, the working head assembly 2 comprises an anvil member 10 coupled to a distal end 12*a* of a housing 12 with a proximal cap 14 coupled to a proximal end 12*b* of the housing. A staple firing mechanism 16 is mounted in the distal end 12*a* so that staples fired therefrom are directed toward a staple-forming surface 10*a* on a proximal side of the anvil member 10. Those skilled in the art will understand that various working head assembly/anvil profiles may be employed depending on the desired line of tissue stapling and cutting for a particular application.

A drive mechanism (described more fully below) moves the anvil member 10 relative to the staple firing mechanism 16 between a first position in which the anvil member 10 is separated from the distal end 12*a* by a predetermined tissue-receiving distance and a second position in which the anvil member 10 is separated from the distal end 12a by a desired stapling distance which is less than the tissue-receiving distance. Those skilled in the art will understand that, for insertion of the device into and retraction of the device from the body lumen, the drive mechanism may also move the anvil member 10 relative to the distal end 12a to a fully closed position in which the proximal side of the anvil member 10 contacts the distal end 12a. The drive mechanism according to the present invention allows the axial length of the working head assembly 2 to be reduced, thereby improving device mobility and allowing the device to be utilized in areas beyond the reach of larger, less mobile FTRD devices.

Specifically, as shown in FIG. 2, when in the tissue receiving position, the anvil member 10 is separated from the distal end 12a by a gap sufficiently large to allow the operator to draw the lesion to be resected thereinto. When the tissue to be resected has been drawn into the gap between the anvil member 10 and the distal end 12a, the operator actuates the drive mechanism to move the anvil member 10 into a desired stapling position in which the anvil member 10 is separated from the distal end 12a by a gap the size of which is selected based on the characteristics of the staples to be used and the staple forming results desired by the operator. Thus, those skilled in the art will understand that the size of this gap may vary depending on the particular application for which the device is designed or, alternatively, may be adjustable by an operator utilizing known staple gap adjustment mechanisms. In the illustrative embodiment shown in FIGS. 3a and 3b, the minimum gap size is controlled by shoulder members 12c which project distally from the distal end 12a. Thus, when the anvil member 10 is moved proximally, a proximal face of the anvil member 10 contacts the shoulder members 12c when the distance between the staple forming surface 10a and the distal end 12a is the desired stapling distance. In this case, the stapling position is the same as the fully closed position.

Figure 3A:
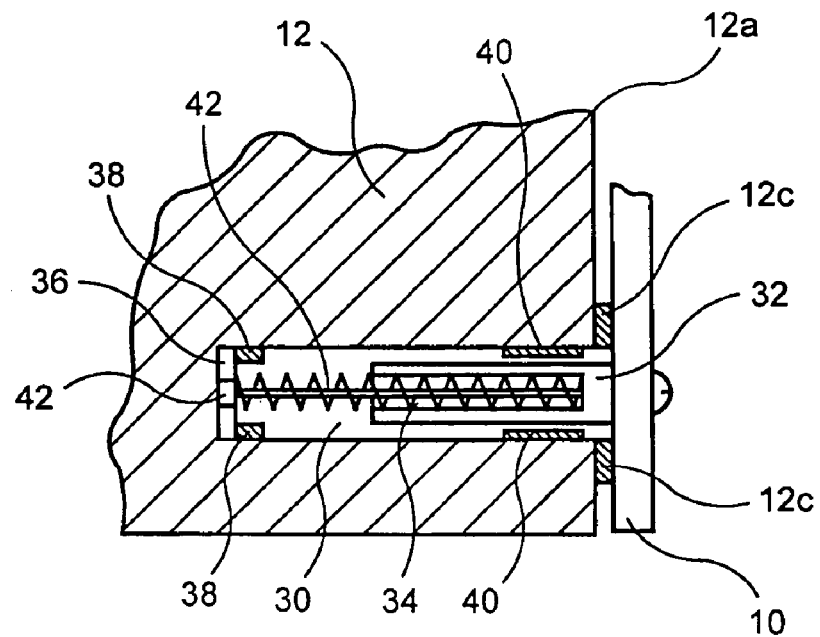
FIG. 3*a* shows a cross-sectional view of the working head assembly of FIG. 2 with the anvil member in a closed position.
Figure 3B:
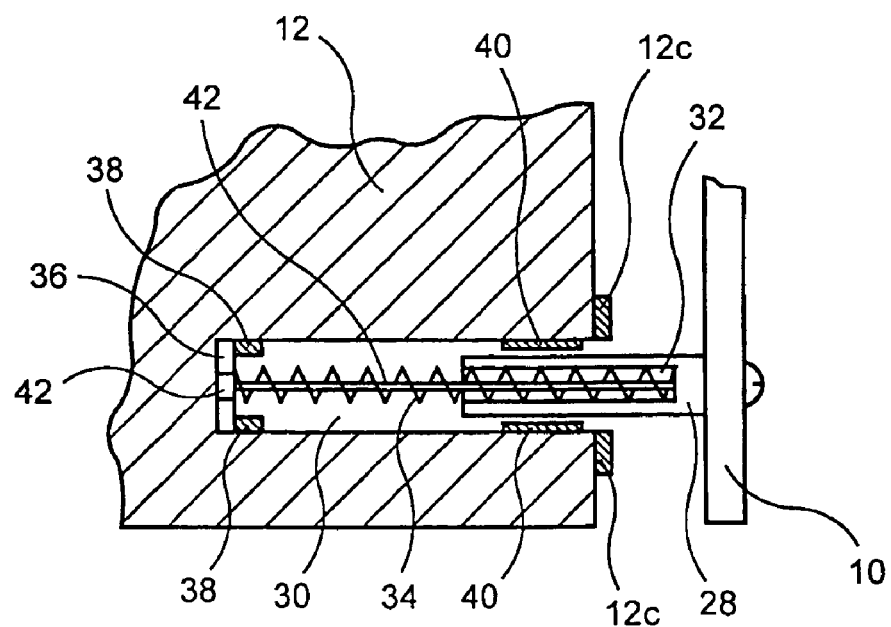
FIG. 3*b* shows a cross-sectional view of the working head assembly of FIG. 2 with the anvil member in an open, tissue receiving position.
Figure 3C:
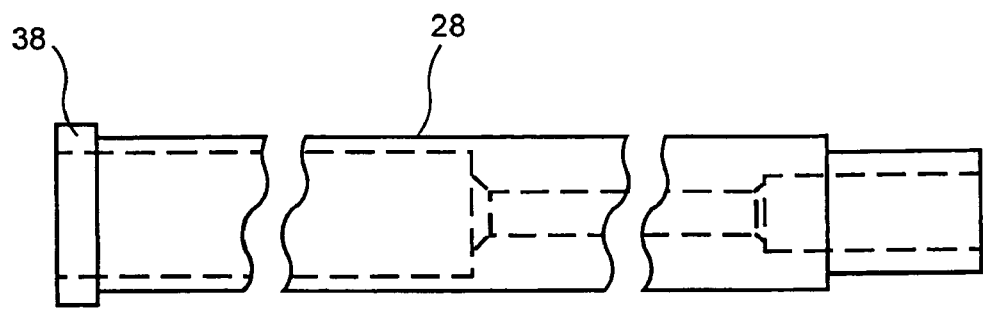
FIG. 3*c* shows a side view of the mounting shaft of FIGS. 3*a* and 3*b*.
Figure 3D:
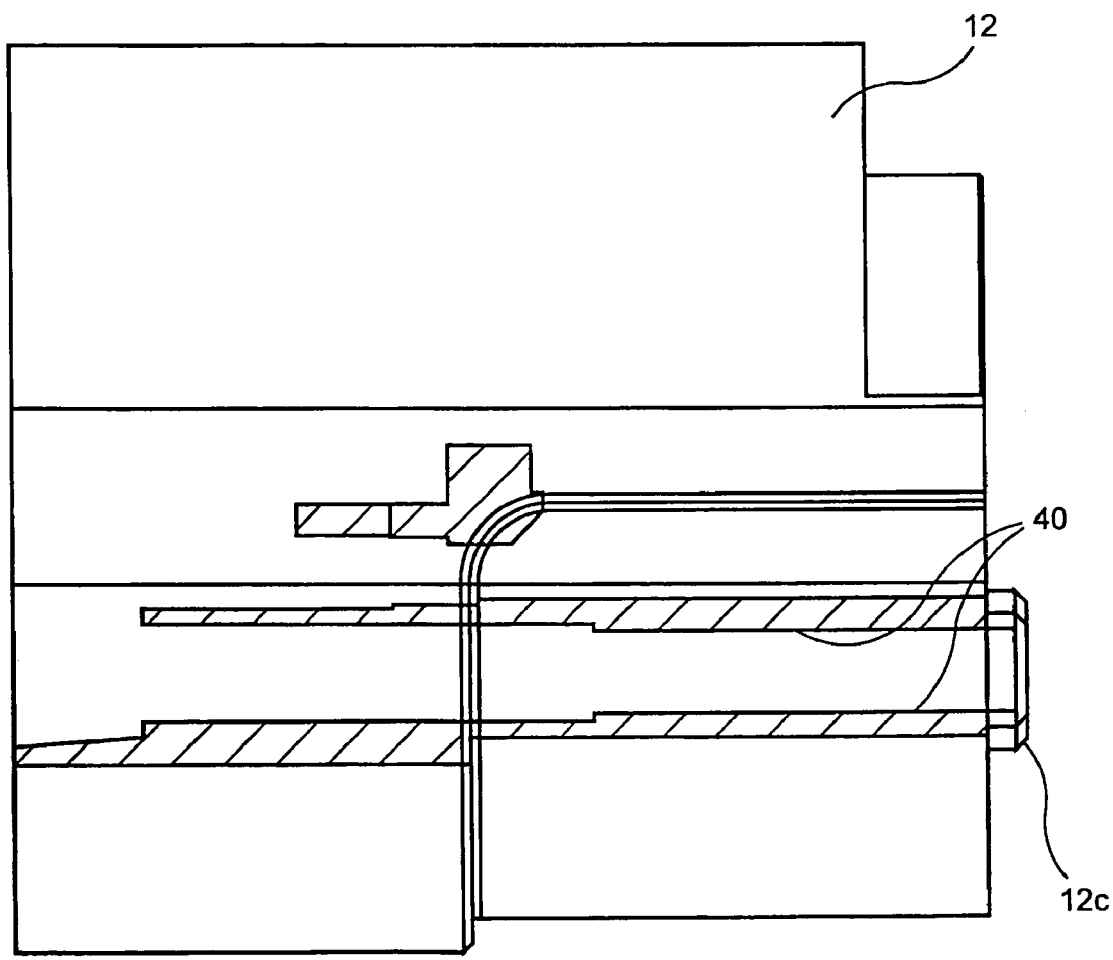
FIG. 3*d* shows a partially cross-sectional view of the working head assembly of FIGS. 3*a* and 3*b* with a more detailed view of the stop surfaces of the housing.

As shown in FIGS. 2, 3a and 3b, the anvil member 10 according to the first illustrative embodiment is coupled to the housing 12 by means of two mounting shafts 28 which are slidably received through corresponding mounting shaft channels 30. Each of the shafts 28 includes a central channel 32 extending therethrough with a compression spring 34 received therein abutting a corresponding spring stop 36 mounted at the proximal end of each of the shaft channels 30. The distal end of each of the springs 34 abuts an inner surface at the distal end of the corresponding central channel 32. Thus, the compression springs 34 bias the anvil member 10 distally away from the distal end 12a of the housing 12. Those skilled in the art will understand that the length of the central channels 32 and the springs 34 should be selected so that, when released, the anvil member 10 is moved distally by the springs 34 away from the distal end 12a to a distance at least equal to the desired tissue receiving gap. In addition, as shown in FIGS. 3c and 3d, an abutting surface 38 may be formed on one or both of the shafts 28 for contacting a corresponding stop surface 40 extending from the housing into the corresponding shaft channel 30 to prevent the anvil member 10 from moving away from the distal end 12a beyond the maximum desired tissue receiving gap.

An anvil control cable 42 is formed as a loop extending from a distal end of a first one of the shafts 28 to which it is coupled, through the corresponding shaft channel 30 and central channel 32 and through the working head assembly 2 proximally into the sheath 4 to pass distally through the sheath 4 to the control handle 6. The loop of the cable 42 extends back through the sheath 4, into the working head assembly 2 to the other shaft 28 via the corresponding shaft channel 30 and central channel 32 to couple to the distal end of that shaft 28. Specifically, the anvil control cable 42 is coupled to the distal ends of each of the control shafts 28 which are coupled to the anvil member 10 and passes as a loop through the sheath 4 to a control cable actuator (not shown) on the control handle 6. Thus, actuating the control cable actuator pulls the loop of the anvil control cable 42 proximally, drawing the anvil member 10 proximally relative to the distal end 12a against the bias of the springs 34. Those skilled in the art will understand that, alternatively, the loop of the anvil control cable 42 may be formed as two separate cables or as a single cable to achieve the same operation. Furthermore, those skilled in the art will understand that the anvil member 10 may be coupled to the housing 12 by a single shaft 28 if desired. However, such a design may provide decreased rigidity.

Thus, actuating the control cable actuator to withdraw the cable(s) 42 proximally from the device while maintaining the position of the working head assembly 2 constant, draws the anvil member 10 proximally toward the distal end 12a of the housing 12. Those skilled in the art will understand that the length of the shaft channels 30, the central channels 32, the guide shafts 30 and the springs 34 should also be selected so that, when the control cable 42 has been withdrawn proximally a maximum distance, the anvil member 10 is moved proximally against the bias of the springs 34 toward the distal end 12a until the anvil member 10 and the distal end 12a are separated by a distance equal to the desired tissue stapling gap. Alternatively, as described above, these components may be designed so that the anvil member 10 may be drawn toward the distal end 12a until the anvil member 10 and the shoulder members 12c are in contact with one another (e.g., a fully closed position for insertion and retraction of the device). As described above, in this embodiment, the stapling position and the fully closed position are the same. As shown in FIGS. 2, 3a and 3b, the thickness of the shoulder members 12c determines the size of the stapling gap. For example, a gap of approximately 0.070" may be employed. However, a separate stapling gap adjusting mechanism may be employed as would be understood by those of skill in the art (e.g., by adjusting the position of the spring stop 36). Furthermore, as would be understood by those of skill in the art, a locking mechanism (not shown) may be included in the control cable actuator to allow a user to lock the cable(s) 42 in a desired position so that a separation of the anvil member 10 and the distal end 12a is held at any desired size.

The compression springs 34 may preferably be formed of stainless steel (e.g., music wire) and should supply a sufficient biasing force to ensure that the anvil member 10 will achieve the desired tissue receiving gap upon release of the control cable actuator, overcoming, for example, any friction resisting distal movement of the shafts 28 and/or the cable(s) 42. For example, a total force of approximately 8 to 12 lbs. and, more preferably approximately 10 lbs., may be sufficient to achieve the preferred tissue receiving gap of 0.75 inches. Thus, each of the springs 34 may, when the anvil member 10 is in the tissue stapling position, have been compressed to the point that a 5 lb. force is applied between the corresponding spring stop 36 and the distal end of the respective central channel 32. For example, a suitable spring for use as the spring 34, may comprise a music wire coil spring with a diameter of, e.g., 0.15 inches with a free length of 1.50 inches such as the commercially available Lee Spring LC-023-AB-14.

Figure 4:
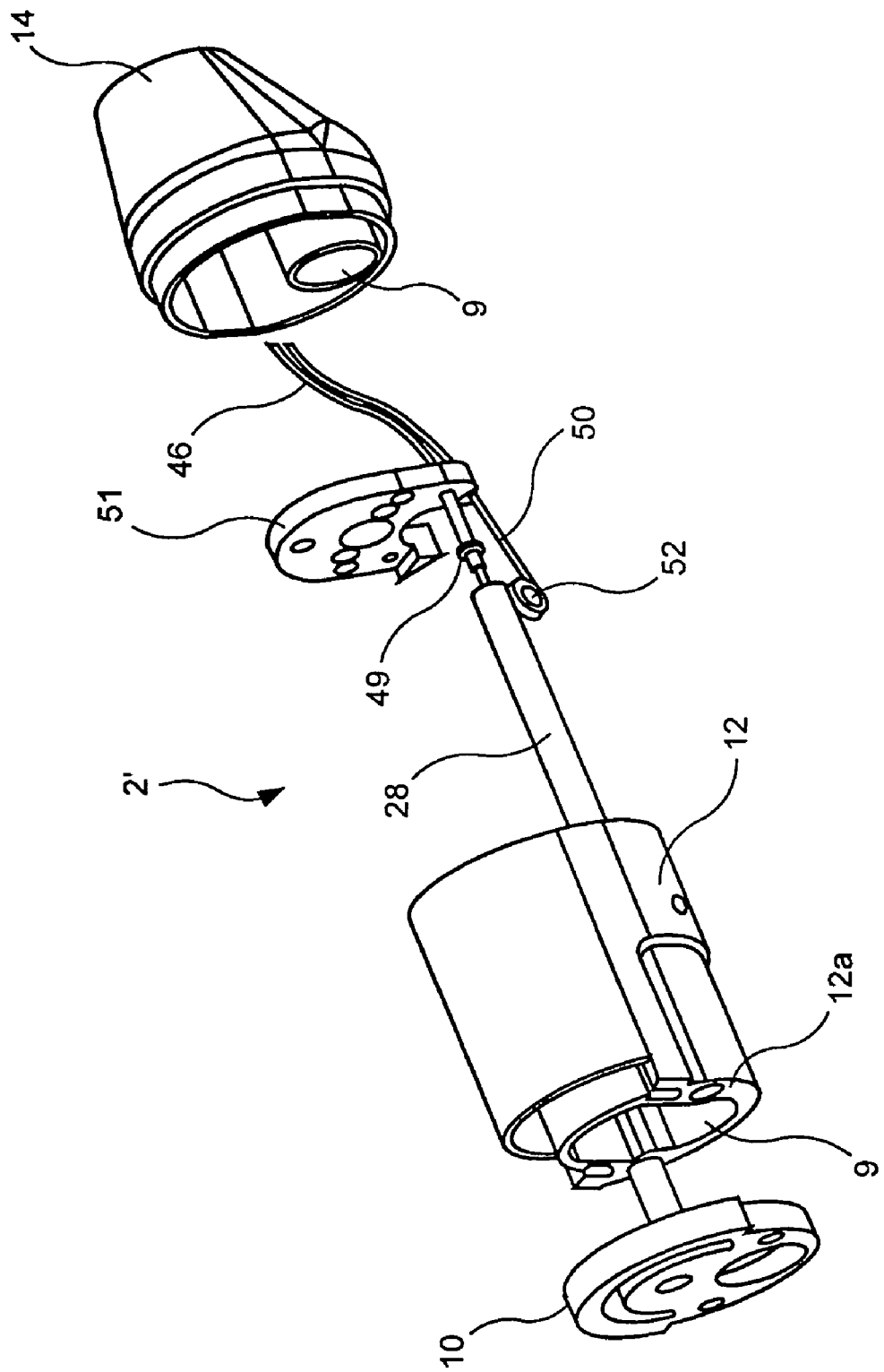
FIG. 4 shows a perspective view of a full thickness resection device according to a second embodiment of the invention.

As shown in FIGS. 4, 5a and 5b, a working head assembly 2' according to a second embodiment of the invention is substantially similar to that of the previously described embodiment except for the drive mechanism which will be described below. The working head assembly 2' includes an anvil member 10 coupled to the distal end 12a of the working head assembly 2' by two shafts 28 received into the working head assembly 2' within corresponding shaft channels 30 as described above in regard to FIGS. 1-3. However, in this embodiment, control cable loops 46 are coupled to the shafts 28, by for example, screws 49 and extend through the sheath 4 to a control cable actuator (not shown) as described above in regard to the control cable 42 of the embodiment shown in FIGS. 1-3. Each of the control cable loops 46 extends from the screw 49, through the corresponding shaft 28, around a pulley 52 back through the working head assembly 2' and the sheath 4 to the control cable actuator as will be described in more detail below. Each of the ends of the cable loops 46 pass through the proximal cap 14 and through a cable routing plate 51 to couple to the corresponding shaft 28.

As shown in FIGS. 5a and 5b, the control cable 46 extends from the control cable actuator (not shown), through the sheath 4 to the working head assembly 2' and is connected to the shaft 28 by a screw 49. The control cable 46 extends from the screw 49 out of the shaft 28 and passes around a pulley 52 to pass out of the working head assembly 2' and through the sheath 4 to the control cable actuator. As would be understood by those of skill in the art, the control cable actuator is designed so that, portions of the cable 46 on opposite sides of the pulley 52 move in opposite directions when the actuator is operated. Each of the pulleys 52 is located distally of the point at which the cable 46 exits the shaft 28 so that, when the control cable actuator is moved so that the cable 46 withdraws the screw 49 and the shaft 28 proximally, the anvil member 10 is moved proximally toward the distal end 12a of the housing 12. Operating the control cable actuator in the opposite direction draws the control cable 46 and the corresponding screw 49 distally so that the shaft 28 and the anvil member 10 are moved distally away from the distal end 12a.

Figure 6:
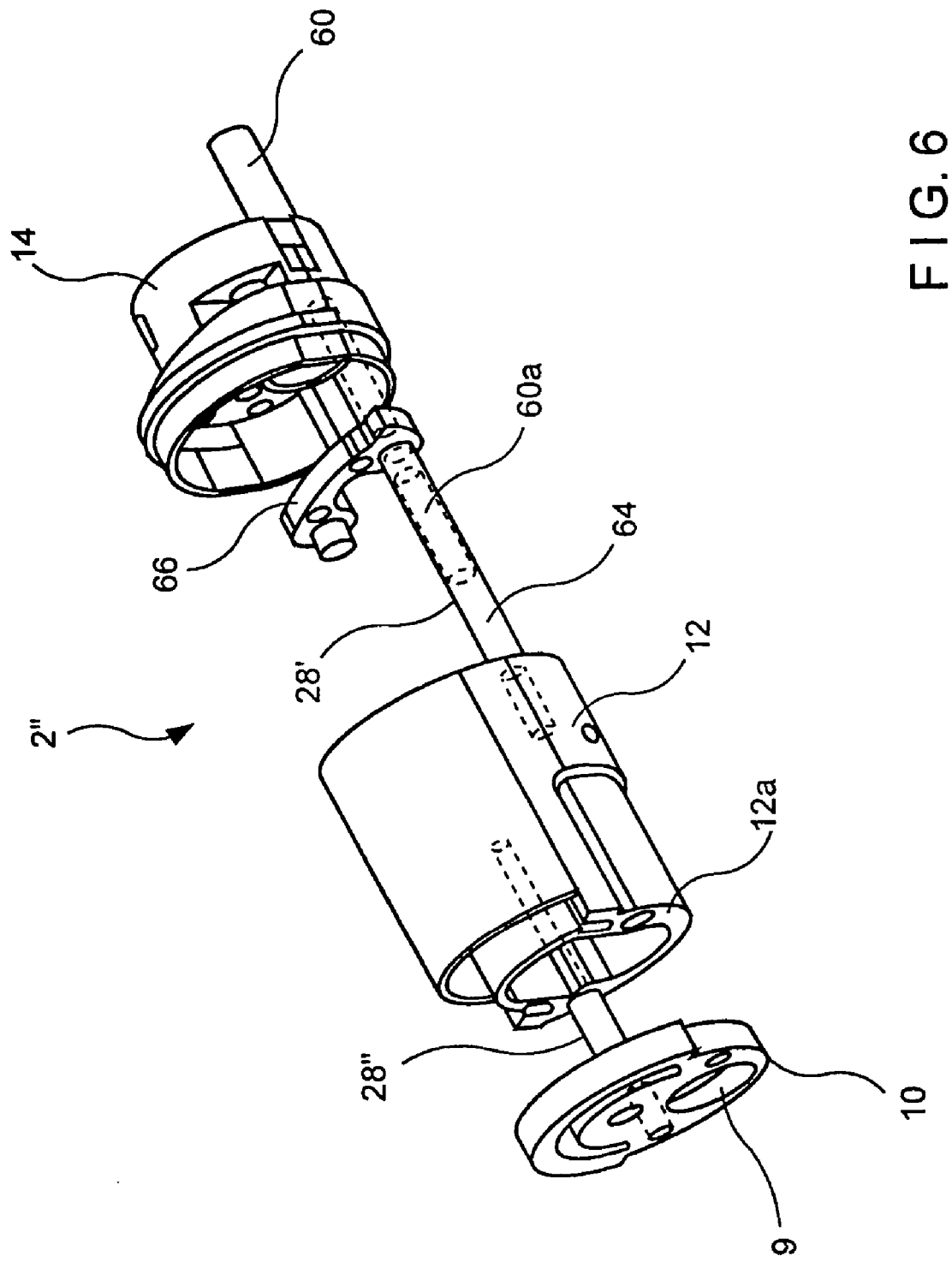
FIG. 6 shows a perspective view of a full thickness resection device according to a third embodiment of the invention.

As shown in FIG. 6, a working head assembly 2" according to a third embodiment of the invention is substantially similar to the previously described embodiments except for the a drive mechanism for moving the anvil member 10 relative to the distal end 12a of the housing 12. Specifically, the drive mechanism of the working head assembly 2" includes an axially flexible, substantially torsionally rigid drive shaft 60 including a threaded distal end 60a which engages a mating thread in a channel 64 extending within a first one of the shafts 28'. The first shaft 28' is coupled to the second of the shafts 28" by a yoke member 66. The first shaft 28' is prevented from rotation relative to the housing 12 by, for example, a projection therefrom fitting into a corresponding recess in the respective shaft channel 30. Thus, as the drive shaft 60 is rotated in a first direction relative to the first shaft 28', the first shaft 28', the yoke member 66 and the second shaft 28" are advanced distally into the housing 12 and the anvil member 10 is moved distally away from the distal end 12a. When the drive shaft 60 is rotated in a second direction opposite to the first direction, the first shaft 28', the yoke member 66 and the second shaft 28" are withdrawn proximally into the housing 12 and the anvil member 10 is drawn toward the distal end 12a.

Figure 7:
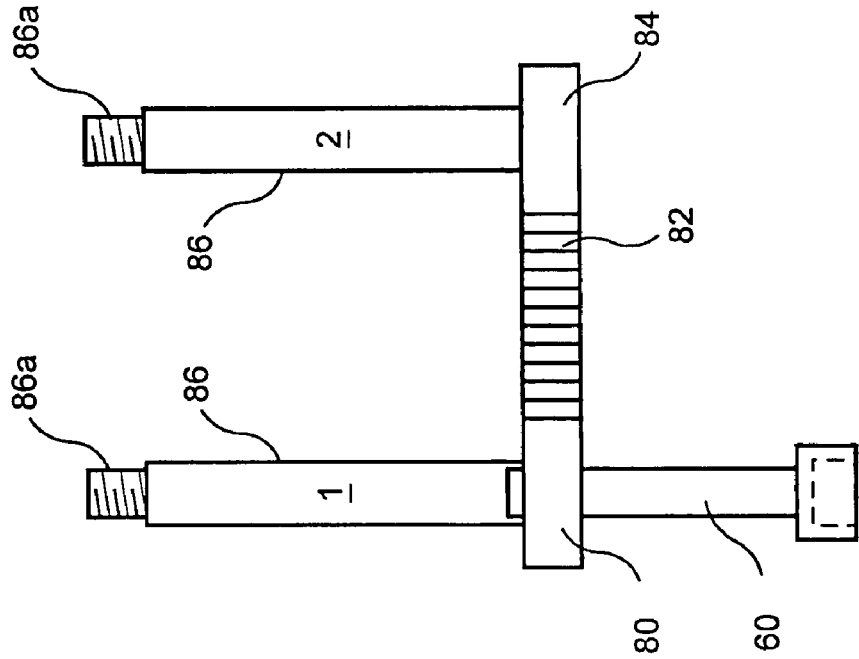
FIG. 7 shows a portion of a drive mechanism according to a fourth embodiment of the invention.

FIG. 7 shows a fourth embodiment of a drive mechanism according to the present invention which is substantially similar to the previously described embodiments except for the a drive mechanism for moving the anvil member 10 relative to the distal end 12a of the housing 12. The drive mechanism of FIG. 7 includes a drive shaft 60 having, for example, a screw member (not shown) mounted thereto. The screw member is received within an idler gear 72 for rotation therewith. The idler gear 72 meshes with gears 74 to rotate shafts 76 which are mounted thereto. Each of the shafts 76 includes a threaded distal portion 76a which engages a mating thread in channels of the shafts 28 (as described above for the mating of shaft 28' and the threaded portion 60a). Thus, upon rotation of the drive shaft 60, the idler gear 72 rotates the gears 74, the shafts 76 and the threaded portions 76a to move the shafts 28 and the anvil member 10 toward and away from the distal end 12a of the housing 12.

Figure 8:
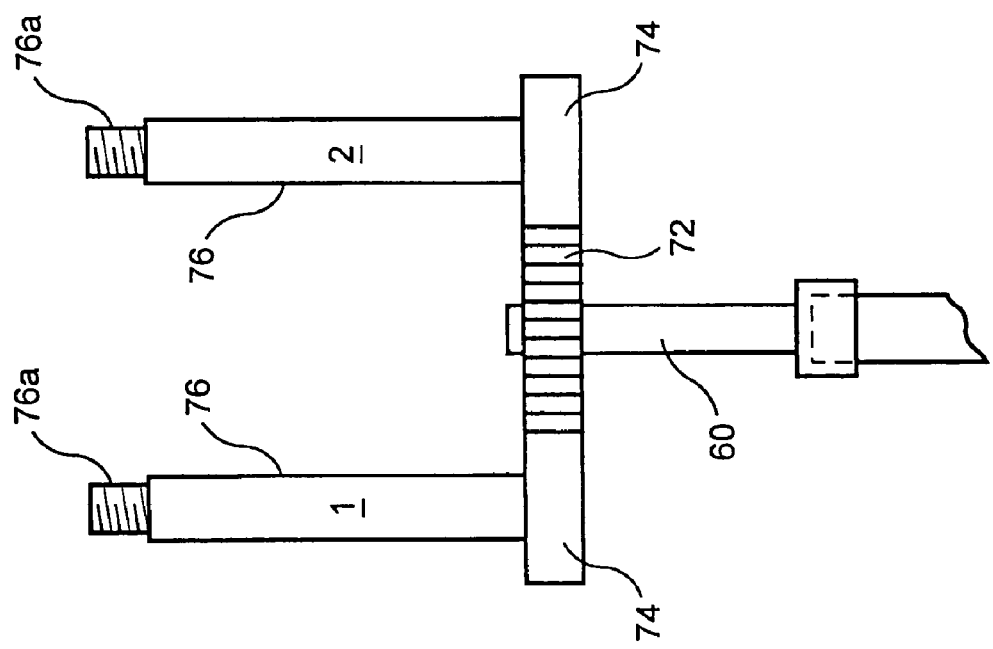
FIG. 8 shows a portion of a drive mechanism according to a fifth embodiment of the invention.

FIG. 8 shows a fifth embodiment of a drive mechanism according to the present invention which is substantially similar to the drive mechanism of the fourth embodiment and the previously described embodiments except for the drive mechanism for moving the anvil member 10 relative to the distal end 12a of the housing 12. The drive mechanism of FIG. 8 includes a drive shaft 60 having a screw member (not shown) mounted thereto. The screw member is received within a first gear 80 for rotation therewith. The first geared shaft 80 meshes with an idler gear 82 to rotate a second gear 84. Rotation of each of the first and second gears 80, 84, in turn, rotates a corresponding one of the shafts 86 mounted thereto. Each of the shafts 86 includes a threaded distal portion 86a which engages a mating thread in a channel of a corresponding one of the shafts 28 (as described above for the mating of shafts 28 and the shafts 74). Thus, upon rotation of the drive shaft 60, the screw member rotates the gear 80, thereby rotating the idler gear 82 and the second gear 84 which rotates the shafts 86 and the threaded portions 86a within the shafts 28 to move the anvil member 10 toward and away from the distal end 12a.

The above described embodiments are for purposes of illustration only and the various modifications of these embodiments which will be apparent are considered to be within the scope of the teachings of this invention which is to be limited only by the claims appended hereto.

What is claimed is:

1. A full thickness resection device comprising:
   a control handle which, when the device is in a working position within a body lumen of a patient, remains outside a body, the control handle including an actuator;
   a working head assembly coupled to the control handle wherein, when the device is in the working position, the working head assembly is located within a body lumen adjacent to a portion of tissue to be resected, the working head assembly including first and second tissue coupling members moveable relative to one another;
   a flexible drive shaft extending from the actuator to the working head assembly;
   a first threaded member coupled to a distal end of the drive shaft for rotation therewith so that, as the drive shaft is rotated, the first threaded member rotates within a threaded channel in a first mounting bar coupled to the first tissue coupling member moving the first mounting bar and the first tissue coupling member relative to the second tissue coupling member;
   a gearing mechanism coupled between the drive shaft and the first threaded member so that rotation of the drive shaft rotates the gearing mechanism which rotates the first threaded member;
   a second mounting bar coupled to the first tissue coupling member and movably received within the working head assembly; and
   a second threaded member received within a threaded channel formed within the second mounting bar, the second threaded member being coupled to the first threaded member via the gearing mechanism so that rotation of the drive shaft rotates the first threaded member to rotate the gearing mechanism which rotates the second threaded member within the threaded channel.

2. The device according to claim 1, wherein the drive shaft is coupled to the first and second threaded members via the gearing mechanism.

* * * * *